United States Patent [19]

Löffel

[11] 4,282,433
[45] Aug. 4, 1981

[54] APPARATUS FOR MEASURING THE DENSITY OF A MULTIPHASE STREAM

[75] Inventor: Rudi Löffel, Karlsruhe, Fed. Rep. of Germany

[73] Assignee: Kernforschungszentrum Karlsruhe GmbH, Karlsruhe, Fed. Rep. of Germany

[21] Appl. No.: 28,671

[22] Filed: Apr. 10, 1979

[30] Foreign Application Priority Data

Apr. 19, 1978 [DE] Fed. Rep. of Germany ....... 2817018

[51] Int. Cl.³ ............................................... G01F 1/00
[52] U.S. Cl. .................................... 250/356; 250/359; 250/435
[58] Field of Search ............... 250/356, 358 R, 432, 250/435, 394, 395, 359; 73/194 M, 32 R

[56] References Cited

U.S. PATENT DOCUMENTS 2,298,942  10/1942  Hicks et al. ............. 250/358 R
3,635,082  1/1972   Prellwitz et al. ............ 73/194 M

FOREIGN PATENT DOCUMENTS 2304618  1/1973  Fed. Rep. of Germany ........... 250/356
2642064  3/1978  Fed. Rep. of Germany ....... 250/358 R Primary Examiner—Davis L. Willis
Assistant Examiner—Carolyn E. Fields
Attorney, Agent, or Firm—Spencer & Kaye

[57] ABSTRACT

A system for measuring the density of a fluid stream by utilization of the gamma ray absorption method, including a flow channel through which the stream is conducted, a source of gamma radiation, which is directed through the channel, and a gamma radiation detector system disposed for receiving gamma radiation after it passes through the channel, with the radiation source being composed of at least two radiation sources disposed in a common plane perpendicular to the axis of the flow channel and angularly spaced about that axis and at least one beam channel associated with each source for forming the radiation from its source into a collimated beam directed into the flow channel, the beam channels being oriented for causing collimated beams from each source to intersect one another within the flow channel.

6 Claims, 2 Drawing Figures

APPARATUS FOR MEASURING THE DENSITY OF A MULTIPHASE STREAM

BACKGROUND OF THE INVENTION

The present invention relates to an apparatus for measuring the density of a single or multiphase stream by utilization of the gamma ray absorption method, the apparatus being of the type in which the single or multiphase stream is conducted through a flow channel and is penetrated or traversed by gamma radiation which is recorded after passage through the stream by one or a plurality of detectors.

In such apparatus, the density of such a stream is determined according to the gamma ray absorption method. The measuring principle is based on the differences in attenuation, or weakening, of the intensity of the gamma radiation during passage through substances having different densities. Thus the intensity of gamma radiation is reduced to a greater degree when the measuring path traverses a flow channel in which only a liquid flows than when it traverses a two-phase liquid-vapor mixture in the flow channel and it is weakened the least when, for example, only vapor is disposed in the measuring path. These differences in weakening of intensity are used as a measure for the amount of vapor, or for the volumetric vapor content, respectively, in the flow channel.

The present invention is primarily concerned with determining the phase distribution states of the type depicted, in longitudinal and axial cross sections, respectively, in FIGS. 1a–1h, which show respective examples of bubble flow in FIG. 1a, varicose flow in FIG. 1b, laminar flow in FIG. 1c, sinuous flow in FIG. 1d, surging flow in FIG. 1e, plugged flow in FIG. 1f, film flow in FIG. 1g and mist flow in FIG. 1h, for the example of a two-phase, gas-liquid stream in a horizontal tube.

SUMMARY OF THE INVENTION

It is an object of the present invention to improve the capabilities of such apparatus.

This and other objects are achieved, according to the invention, in a system for measuring the density of a fluid stream by utilization of the gamma ray absorption method, including means defining a flow channel through which the stream is conducted, gamma radiation source means for directing gamma radiation through the channel, and gamma radiation detector means disposed for receiving gamma radiation after it passes through the channel, by constituting the source means of at least two radiation sources disposed in a common plane perpendicular to the axis of the flow channel and angularly spaced about the axis and means defining at least one beam channel associated with each source for forming the radiation from its source into a collimated beam directed into the flow channel, the beam channels being oriented for causing collimated beams from each source to intersect one another within the flow channel. The two sources being offset one another are necessary similar to optics to obtain a stereo-pair. With the diverging beam paths it is than possible to get a definition in depth.

A particularly advantageous feature of apparatus according to the present invention for measuring the density of single or multiphase streams resides in the provision of two density measuring systems which are spaced from one another with respect to the flow channel axis to measure the mass flow. For simpler phase distribution states than described above with reference to FIG. 1, fewer than three beam channels per source will suffice. If the measuring results are to be refined or must be extremely precise, the number of beam channels, and with it the number of detectors, for each measuring device must be increased.

DESCRIPTION OF THE PREFERRED EMBODIMENTS

Figure 1:
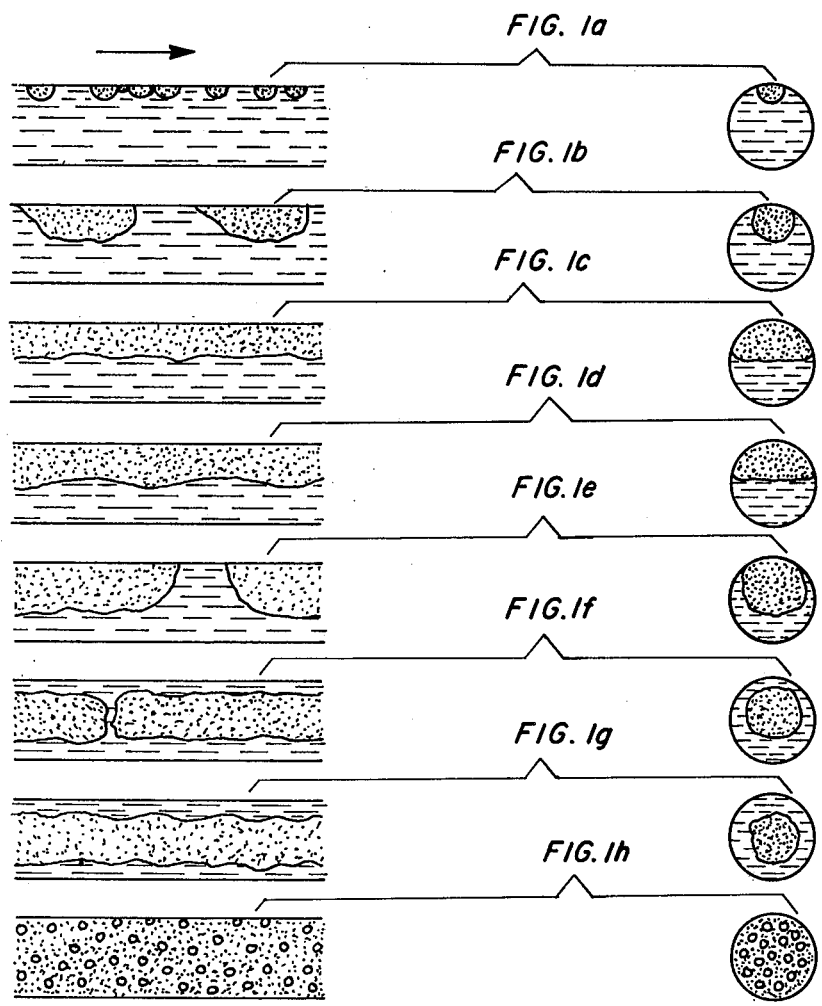
FIGS. 1a to 1h are pictorial views, in longitudinal and axial cross section, of exemplary types of two-phase flows which can be measured according to the invention, which Figures have already been described above.
Figure 2:
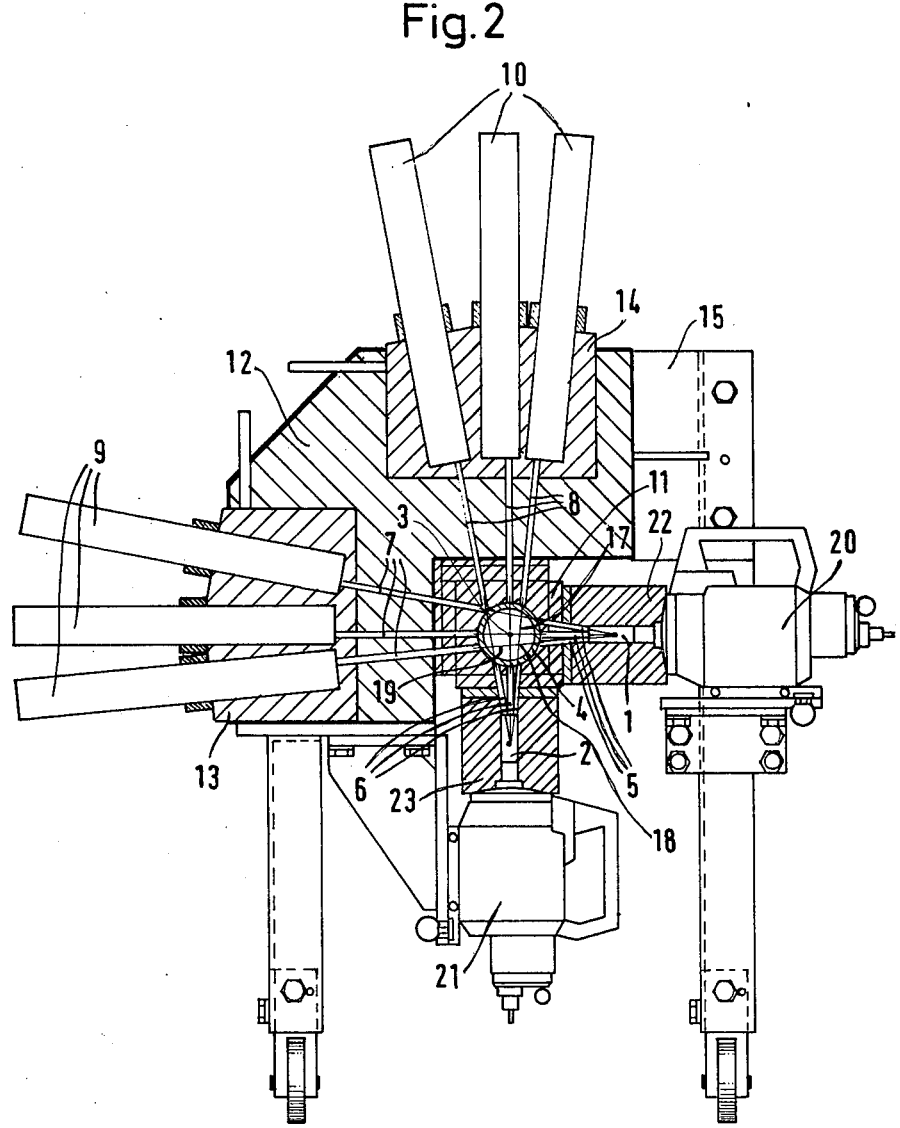
FIG. 2 is a cross-sectional, elevational view of a preferred embodiment of the invention, taken in a plane perpendicular to the axis of a flow channel enclosing the stream to be measured.

The density measuring system shown in FIG. 2 is composed essentially of two dot-shaped gamma radiation sources 1 and 2, which are angularly (90° one to another) offset with respect to one another about the axis 3 of flow channel 4. These sources can be transported in respective lockable shielding containers 20 and 21 and are surrounded by respective collimators 22 and 23. The collimators are connected to a flow channel 4 which has a circular inner cross section and is formed by walls that have flat exterior sides and give channel 4 a square exterior cross section. At the side of the flow channel axis 3 opposite each source 1 and 2, three detectors 9 or 10, respectively, are provided for each source. The detectors associated with each source have their frontal faces directed toward the associated source and are shielded against stray radiation or radiation from the environment by means of shields 11, 12, 13 and 14, which are fastened to a movable frame 15, as are the transporting containers 20 and 21 and the flow channel 4.

Three narrow beam channels 5 emanate in the shape of a fan from the dot-shaped gamma radiation source 1 and three narrow beam channels 6 similarly emanate from source 2, all in the direction toward the flow channel 4, thus forming two sets of collimated beams 17 and 19, respectively, which pass through the flow channel 4 in a plane perpendicular to the axis 3 of flow channel 4. Beams 17 and 19 intersect one another at points 18. After passing through the flow channel 4, the beams enter into further beam channels 7 and 8 which are connected to detectors 9 and 10, respectively.

In order to measure the density or the mass flow, respectively, in channel 4, for which purpose two density measuring systems, each having the form shown in FIG. 2, must be provided and spaced apart along the flow channel axis 3, the two gamma radiation sources 1 and 2 are moved from the lockable shielding containers 20 and 21 into the collimators 22 and 23. The latter are made of lead or some other material having a good shielding effect against gamma radiation and their dimensions are selected so that not only the radiation load in their immediate vicinity remains at a low level and stray radiation which could interfere with the measurement is substantially avoided, but also so that the gamma radiation is collimated in collimator bores or beam channels 5 through 8, respectively, so as to pass through the flow channel 4. The further shielding 12, 13 and 14 serves to further eliminate stray radiation.

In order to be able to operate the system also at higher temperatures of the flowing medium or of the environment, cooling by means of water, air or some other coolant, is provided for the more sensitive parts.

The gamma radiation sources 1 and 2 are preferably dot-shaped $Ir^{192}$ or $Cs^{137}$ isotope sources. A certain proportion of the gamma quanta emitted by the radiation source 1 and 2, respectively, impinges on the frontal faces of detectors 9 and 10, respectively, and there generates flashes of light in a scintillation crystal. These pulses are electronically amplified in a known manner and are processed in analog form or recorded, respectively.

With the above-mentioned positioning of two such multiple beam density measuring systems, each constituting a structure as shown in FIG. 2, so that they are spaced apart along the axis 3, it is possible to measure in addition to the density and phase distribution, also the travel times of the individual phases by way of cross-correlation of the density signals. For this purpose an analog correlator is used (not shown) or a PDPM Computer System (Digital Equipments, U.S.) The mass flow of the single or multiphase stream in flow channel 4 can then be determined from the speed and density measurements.

The combination of two sources used in illustrated embodiments, each with three beam channels, with one detector per beam channel and an angled arrangement of the beam channels with respect to one another, and the position of the sources with respect to one another were determined or optimized, respectively, experimentally and by way of calculations for a flow channel having a diameter $d = 50$ mm. The same applies for the location of the points of intersection of the beam axes in the beam channels within the flow channel. The deviation of the external beams from the central beam is 5'46" and 10'43".

It will be understood that the above description of the present invention is susceptible to various modifications, changes and adaptations, and the same are intended to be comprehended within the meaning and range of equivalents of the appended claims.

What is claimed is:

1. In a system for measuring the denisty of a two-phase, gas-liquid fluid stream by utilization of the gamma ray absorption method, including means defining a flow channel through which the stream is conducted, gamma radiation source means for directing gamma radiation through the channel, and gamma radiation detector means disposed for receiving gamma radiation after it passes through the channel, the improvement wherein said source means comprises at least two radiation sources disposed in a common plane perpendicular to the axis of said flow channel and angularly spaced about that axis and means defining at least one beam channel associated with each said source for forming the radiation from its said source into a collimated beam directed into said flow channel, said beam channels being oriented for causing collimated beams from each said source to intersect one another within said flow channel.

2. An arrangement as defined in claim 1 wherein said means defining at least one beam channel present three beam channels for each said radiation source, with said beam channels for each said source forming three collimated beams which diverge from one another in a fan pattern, with each beam from one said source intersecting at least one beam from the other said source in said flow channel.

3. An arrangement as defined in claim 2 wherein said detector means comprise a plurality of radiation detectors each associated with a respective beam channel and each disposed at the opposite side of said flow channel from that one of said sources which is associated with its respective beam channel, and each said beam channel is continued from such opposite side of said flow channel toward its associated radiation detector.

4. An arrangement as defined in claim 1, 2 or 3 further comprising means shielding said radiation sources and said detectors with respect to radiation from the environment and stray radiation.

5. An arrangement as defined in claim 4 further comprising a movable frame to which said shielding means, said flow channel defining means, said radiation sources and said detectors are fastened.

6. Apparatus for measuring the mass flow of a fluid stream flowing through a flow channel, comprising two systems for measuring the density of a two-phase, gas-liquid fluid stream each as defined in claim 1, spaced apart from one another along the axis of said flow channel.

* * * * *